(12) United States Patent
Pai

(10) Patent No.: US 8,267,282 B2
(45) Date of Patent: Sep. 18, 2012

(54) QUANTITATIVE DROPPER STRUCTURE

(76) Inventor: Hsi-Wen Pai, Chiayi (TW)

( * ) Notice: Subject to any disclaimer, the term of this patent is extended or adjusted under 35 U.S.C. 154(b) by 385 days.

(21) Appl. No.: 12/755,004

(22) Filed: Apr. 6, 2010

(65) Prior Publication Data

US 2011/0240674 A1    Oct. 6, 2011

(51) Int. Cl.
*B67D 7/78* (2010.01)
(52) U.S. Cl. ........ 222/158; 222/205; 222/207; 222/211; 222/464.1; 141/35
(58) Field of Classification Search ............ 141/35–36, 141/230; 222/158, 204–205, 207, 211, 436, 222/438, 284, 454–457, 464.1
See application file for complete search history.

(56) References Cited

U.S. PATENT DOCUMENTS

| | | | | |
|---|---|---|---|---|
| 2,730,270 A | * | 1/1956 | Heinemann | 222/205 |
| 3,064,863 A | * | 11/1962 | Mattson | 222/205 |
| 3,089,623 A | * | 5/1963 | Padzieski | 222/205 |
| 3,438,551 A | * | 4/1969 | Belisle | 222/182 |
| 3,661,288 A | * | 5/1972 | Noll | 215/11.1 |
| 3,811,484 A | * | 5/1974 | Engelbrecht | 141/7 |
| 4,171,075 A | * | 10/1979 | Gangwisch | 222/456 |
| 4,957,218 A | * | 9/1990 | Ford, Jr. | 222/1 |
| 5,988,456 A | * | 11/1999 | Laible | 222/464.1 |
| 6,186,367 B1 | * | 2/2001 | Harrold | 222/205 |
| 6,330,960 B1 | * | 12/2001 | Faughey et al. | 222/205 |

* cited by examiner

*Primary Examiner* — Kevin P Shaver
*Assistant Examiner* — Andrew P Bainbridge
(74) *Attorney, Agent, or Firm* — Guice Patents PLLC

(57) ABSTRACT

A quantitative dropper structure includes a resilient bottle body, a nozzle detachably sealingly connected to a bottle opening of the bottle body, and a transfer mechanism having a flow path formed of a first transfer pipe, a remaining liquid reservoir and a second transfer pipe. The nozzle has a dispensing orifice and a bottom wall formed with a perforation. The first transfer pipe has a first end communicating with the remaining liquid reservoir and a second end downward extending near to a bottom section of the bottle body. The second transfer pipe has a front end passing through the perforation to communicate with the liquid reservoir and a rear end communicating with the remaining liquid reservoir. When compressed, the liquid flows in the flow path into the liquid reservoir. After a predetermined volume of liquid is contained in the liquid reservoir, the liquid is quantitatively dispensed from the dispensing orifice.

20 Claims, 15 Drawing Sheets

QUANTITATIVE DROPPER STRUCTURE

BACKGROUND OF THE INVENTION

1. Field of the Invention

The present invention relates generally to a graduated container, and more particularly to a quantitative dropper structure.

2. Description of the Related Art

A conventional squeeze dropper bottle for containing liquid medicine generally has a conic tip formed with a dispensing orifice. A tiny amount of liquid can be dispensed from the dispensing orifice of the squeeze dropper bottle. For example, a total dispensed amount of 1 cc of liquid needs 18 droplets. A user can compress the bottle body of the dropper bottle to dispense a droplet or droplets according to the required total dose. However, it is hard for the user to stably control the total amount of the dispensed liquid. In the case that the bottle body is over-compressed, an excessive amount of liquid may be dispensed from the dispensing orifice. Therefore, the dose of the liquid can be hardly precisely controlled. In practical medicine dosage such as vaccination or nutrition supplement, a larger amount of liquid medicine, for example, 3 cc of liquid medicine, may need to be dispensed according to the properties thereof In this case, a user needs to pay more attention to the control of magnitude of compression force and the number of the dispensed droplets. Otherwise, a tiny mistake may lead to a serious consequence. An underdose can hardly achieve a desired effect. An overdose will result in waste of liquid medicine or even intoxication in some more serious cases.

SUMMARY OF THE INVENTION

It is therefore a primary object of the present invention to provide a quantitative dropper structure, which can quantitatively dispense droplets at constant amount under precise control. Moreover, a larger amount of liquid can be constantly dispensed at one time to greatly reduce the use of the burette and graduated cup.

It is a further object of the present invention to provide the above quantitative dropper structure, which can conveniently and precisely dispense a larger amount of liquid.

To achieve the above and other objects, the quantitative dropper structure of the present invention includes a resilient bottle body, a nozzle and a transfer mechanism. The resilient bottle body is compressible, having a bottle opening at a top end. The nozzle is detachably and sealingly connected to the bottle opening The nozzle is formed with a liquid reservoir for containing a liquid therein. The nozzle is transparent or translucent for a user to observe and check the volume of the liquid contained in the nozzle. The nozzle has a tip formed with a dispensing orifice. The nozzle further has a bottom wall formed with a perforation. The transfer mechanism is received in the bottle body and connected to the nozzle. The transfer mechanism provides a flow path formed of a first transfer pipe, a remaining liquid reservoir and a second transfer pipe. The remaining liquid reservoir is formed with an internal remaining liquid chamber for containing remaining liquid therein. The first transfer pipe is received in the bottle body. A first end of the first transfer pipe is connected to the remaining liquid reservoir in communication with the remaining liquid chamber. A second end of the first transfer pipe downward extends to a position near a bottom section of the bottle body. The second transfer pipe at least has a front end and a rear end. The front end of the second transfer pipe passes through the perforation of the bottom wall of the nozzle and extends into the liquid reservoir thereof The rear end of the second transfer pipe extends into the remaining liquid reservoir to a position near the bottom wall of the remaining liquid reservoir in communication with the remaining liquid chamber.

When compressing the bottle body, the liquid is driven to forward flow in the flow path into the liquid reservoir of the nozzle. After a necessary dose of liquid is contained in the liquid reservoir of the nozzle, the liquid is quantitatively dispensed from the dispensing orifice at constant amount.

According to the above quantitative dropper structure, a user can previously fill a constant amount of liquid into the nozzle for later dispensing. Therefore, the liquid can be dispensed at constant dose under precise control to reduce the use of the burette and graduated cup.

According to the above quantitative dropper structure, the remaining liquid is temporarily reserved in the remaining liquid chamber without mixing with the constant amount of liquid contained in the nozzle. Therefore, the dose of the liquid will not be affected and the droplets can be dispensed at constant amount.

According to the above quantitative dropper structure, a user can first accumulate the liquid in the nozzle to a desired dose and then dispense the liquid at one time. Accordingly, it is unnecessary for the user to repeatedly compress the bottle body and to troublesomely count the number of times of compression. Therefore, a larger amount of liquid can be constantly dispensed at one time to greatly reduce the use of the burette and graduated cup.

The present invention can be best understood through the following description and accompanying drawings, wherein:

DETAILED DESCRIPTION OF THE PREFERRED EMBODIMENTS

Figure 1:
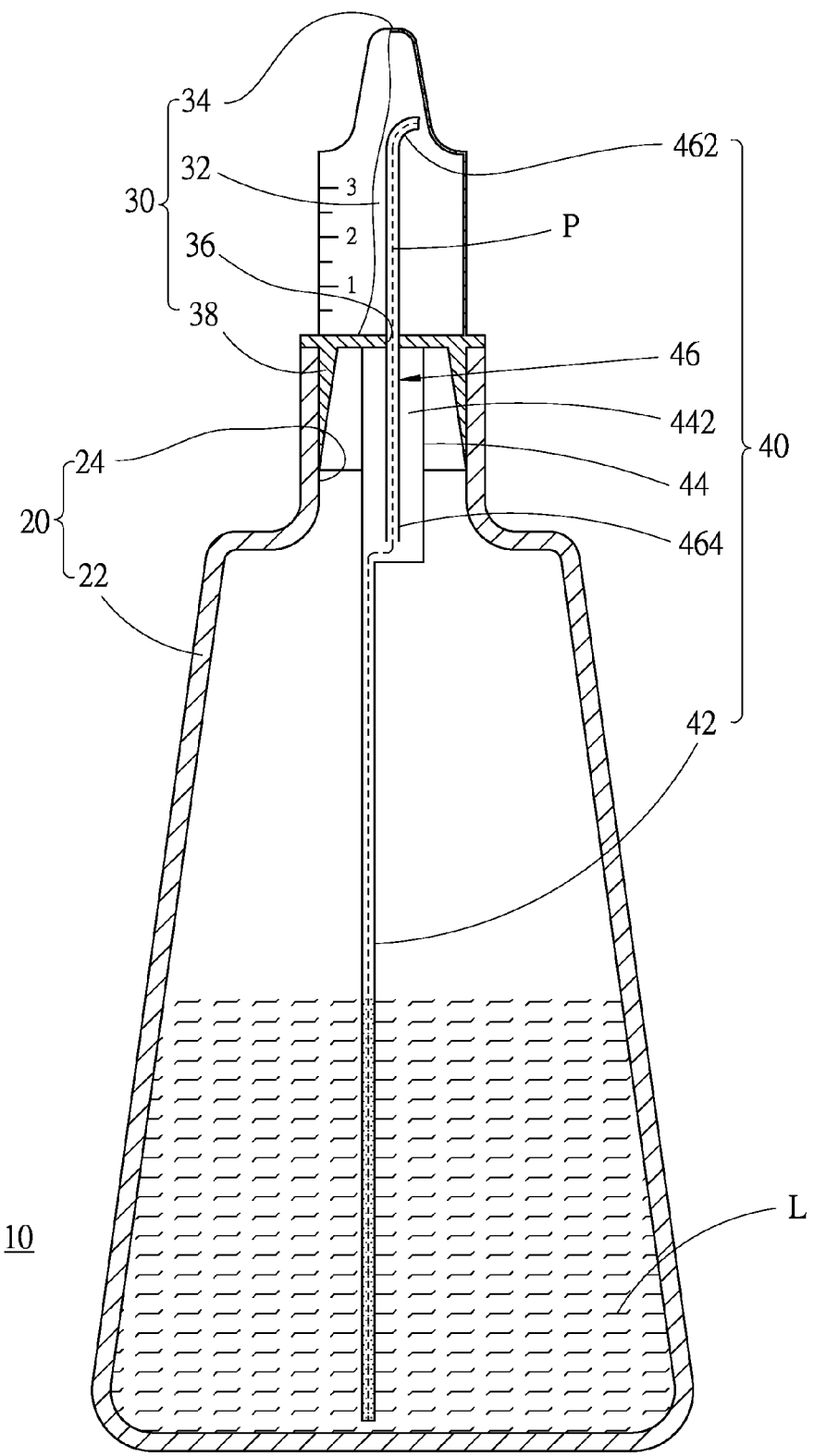
FIG. 1 is a sectional view of a first embodiment of the quantitative dropper structure according to the present invention.
Figure 2:
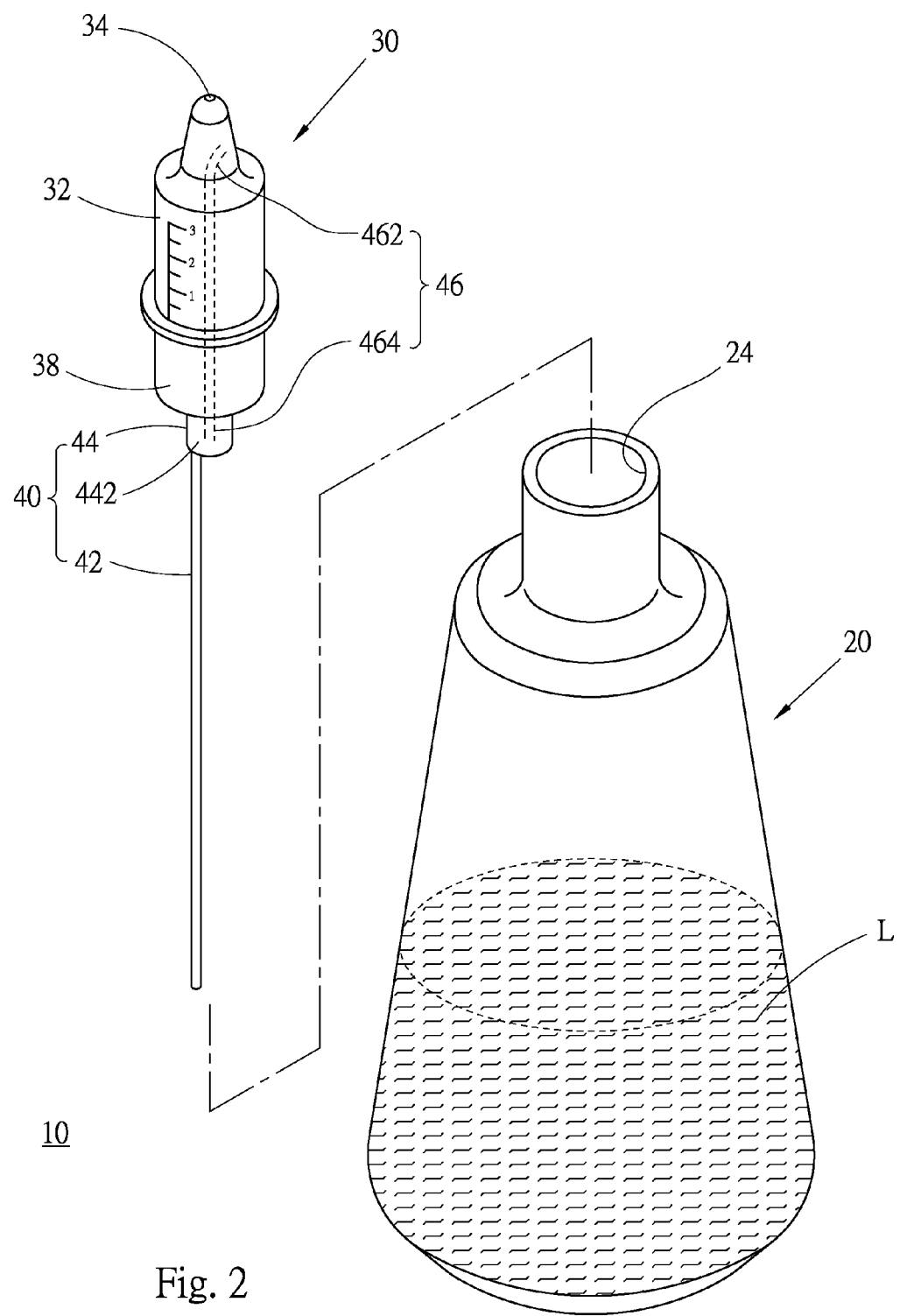
FIG. 2 is a perspective exploded view of the first embodiment of the quantitative dropper structure according to the present invention.

Please refer to FIGS. 1 and 2. According to a first embodiment, the quantitative dropper structure 10 of the present invention includes a resilient bottle body 20, a nozzle 30 and a transfer mechanism 40.

The resilient bottle body 20 is hollow for containing a liquid L therein. The resilient bottle body 20 has a resilient wall 22, which is compressible. A bottle opening 24 is flat and formed at a top end of the resilient bottle body 20 in connection with the nozzle 30. Preferably, the bottle opening 24 has an inner diameter smaller than that of the resilient bottle body 20.

The nozzle 30 is detachably and sealingly connected to the bottle opening 24. The nozzle 30 is formed with a liquid reservoir 32 for containing the liquid therein. The nozzle 30 is translucent or transparent for a user to observe and check the volume of the liquid contained in the nozzle 30. The nozzle 30 has a sharp conic top section to form a tip. The tip is formed with a dispensing orifice 34. The nozzle 30 further has a bottom wall formed with a perforation 36. An annular fitting section 38 is formed under the bottom wall of the nozzle 30 for fitting into the bottle opening 24 of the resilient bottle body 20. The fitting section 38 has, but not limited to, a cylindrical configuration. The fitting section 38 is plugged into the bottle opening 24 to sealingly connect the nozzle 30 to the resilient bottle body 20. A circumference of the nozzle 30 is marked with scales to a user to check the volume of the liquid and precisely know the dose. The nozzle 30 can be dimensioned as desired. The nozzle 30 can be removed by means of unplugging the fitting section 38 out of the bottle opening 24. Therefore, a user can replace the nozzle 30 with another complying with the actual requirement.

The transfer mechanism 40 is connected to the nozzle 30 to provide a flow path P sequentially formed of a first transfer pipe 42, a remaining liquid reservoir 44 and a second transfer pipe 46.

The remaining liquid reservoir 44 is formed with an internal remaining liquid chamber 442 for containing the remaining liquid therein. The remaining liquid reservoir 44 is suspended in the bottle body 20. Alternatively, the remaining liquid reservoir 44 is suspended from the bottom wall of the nozzle 30 with a top face of the remaining liquid reservoir 44 affixed to a bottom section of the nozzle 30.

The first transfer pipe 42 is an elongated pipe received in the bottle body 20 and positioned outside the remaining liquid reservoir 44. A top end of the first transfer pipe 42 is connected to a bottom end of the remaining liquid reservoir 44 in communication with the remaining liquid chamber 442. A bottom end of the first transfer pipe 42 downward extends to a position near a bottom section of the bottle body 20.

In the first embodiment, the second transfer pipe 46 at least has a front end 462 and a rear end 464. The front end 462 extends from the remaining liquid chamber 442 through the perforation 36 of the bottom wall of the nozzle 30 into the liquid reservoir 32 thereof. The rear end is positioned in the remaining liquid reservoir 44 and extends to a position near the bottom wall thereof in communication with the remaining liquid chamber 442.

The front end 462 of the second transfer pipe 46 passes through the perforation 36 of the bottom wall of the nozzle 30 and extends to a position near the sharp conic top section of the nozzle 30. Consequentially, the front end 462 of the second transfer pipe 46 extends into the nozzle 30 by a sufficient length so as to avoid unexpected backflow of the liquid due to insufficient length. The front end 462 of the second transfer pipe 46 can be further curved toward an inner face of the nozzle 30. Such configuration has the following advantages: First, when the liquid contained in the liquid reservoir 32 of the nozzle 30 exceeds a predetermined amount, the curved front end 462 of the second transfer pipe 46 will facilitate backflow of the liquid more easily than a straight one and will keep the liquid contained in the liquid reservoir 32 at a constant predetermined amount. Second, when the liquid flows, the liquid will be first injected to the inner face of the nozzle 30 to flow down along the inner face. Third, when the liquid is injected from the front end 462 of the second transfer pipe 46, the liquid is prevented from being directly injected out of the dispensing orifice 34. To prevent the liquid from being directly injected out of the dispensing orifice 34, optionally, the exit of the front end 462 of the second transfer pipe 46 is not lined up with the dispensing orifice 34. That is, in axial direction of the dropper structure, the exit of the front end 462 of the second transfer pipe 46 is misaligned from the dispensing orifice 34, not positioned right below the dispensing orifice 34.

Please refer to FIGS. 3A to 3D, which show the use of the first embodiment of the quantitative dropper structure 10 according to the present invention.

Figure 3A:
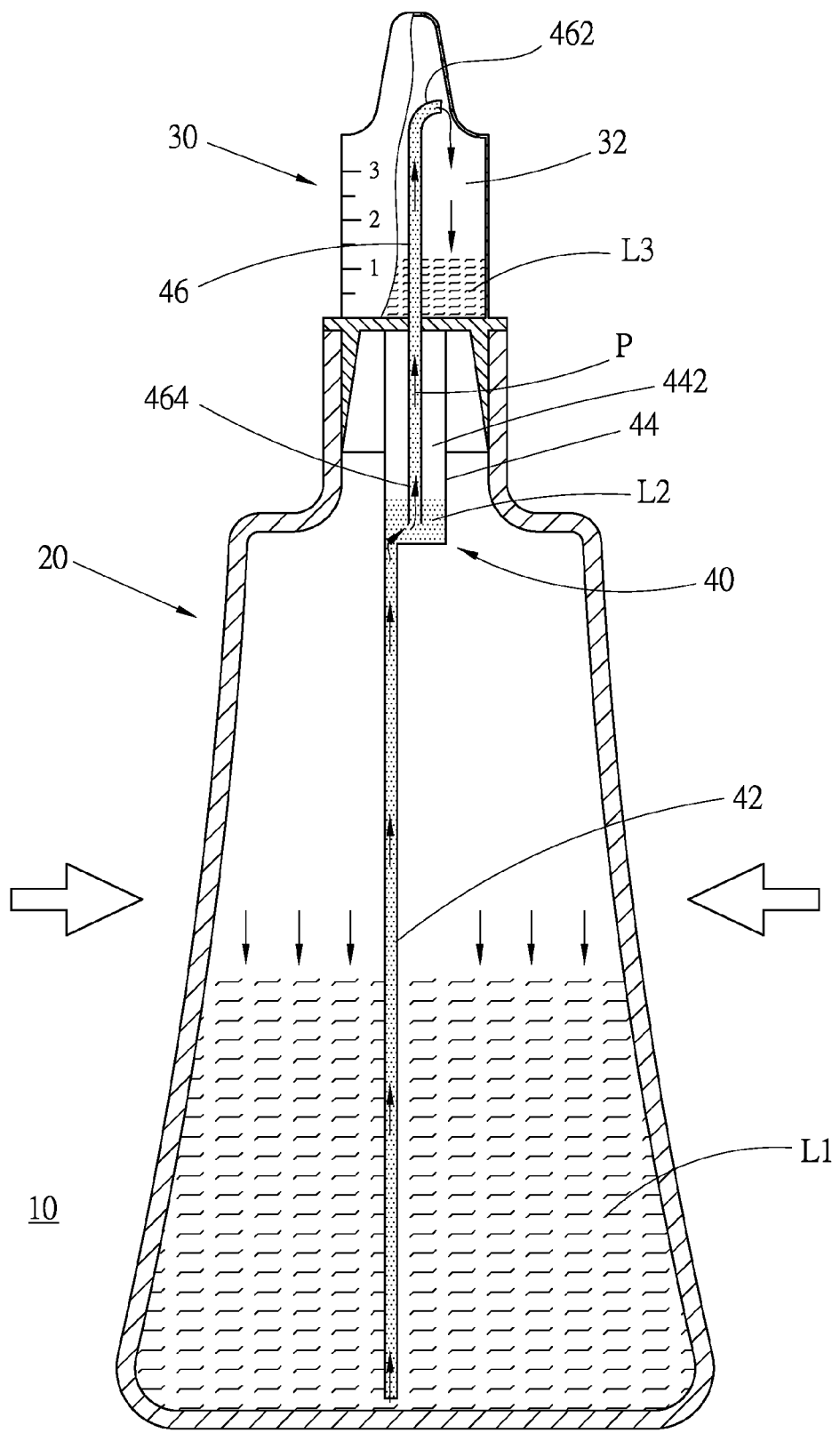
FIGS. 3A to 3D show the use of the first embodiment of the quantitative dropper structure according to the present invention.

As shown in FIG. 3A, when compressing the resilient bottle body 20 to contract the resilient wall 22 of the bottle body 20, the air inside the bottle body 20 is pressurized so that the internal air pressure is higher than the external air pressure. At this time, the pressurized air drives the liquid L1 contained in the bottle body 20 to forward flow in the flow path P, which is formed of the first transfer pipe 42, the remaining liquid reservoir 44 and the second transfer pipe 46, into the liquid reservoir 32 of the nozzle 30. During flowing of the liquid, a certain amount of flowing liquid L2 is reserved in the remaining liquid chamber 442 of the remaining liquid reservoir 44. A user can observe the scales of the nozzle 30 to truly know the volume of the liquid L3 to be dispensed.

Figure 3B:
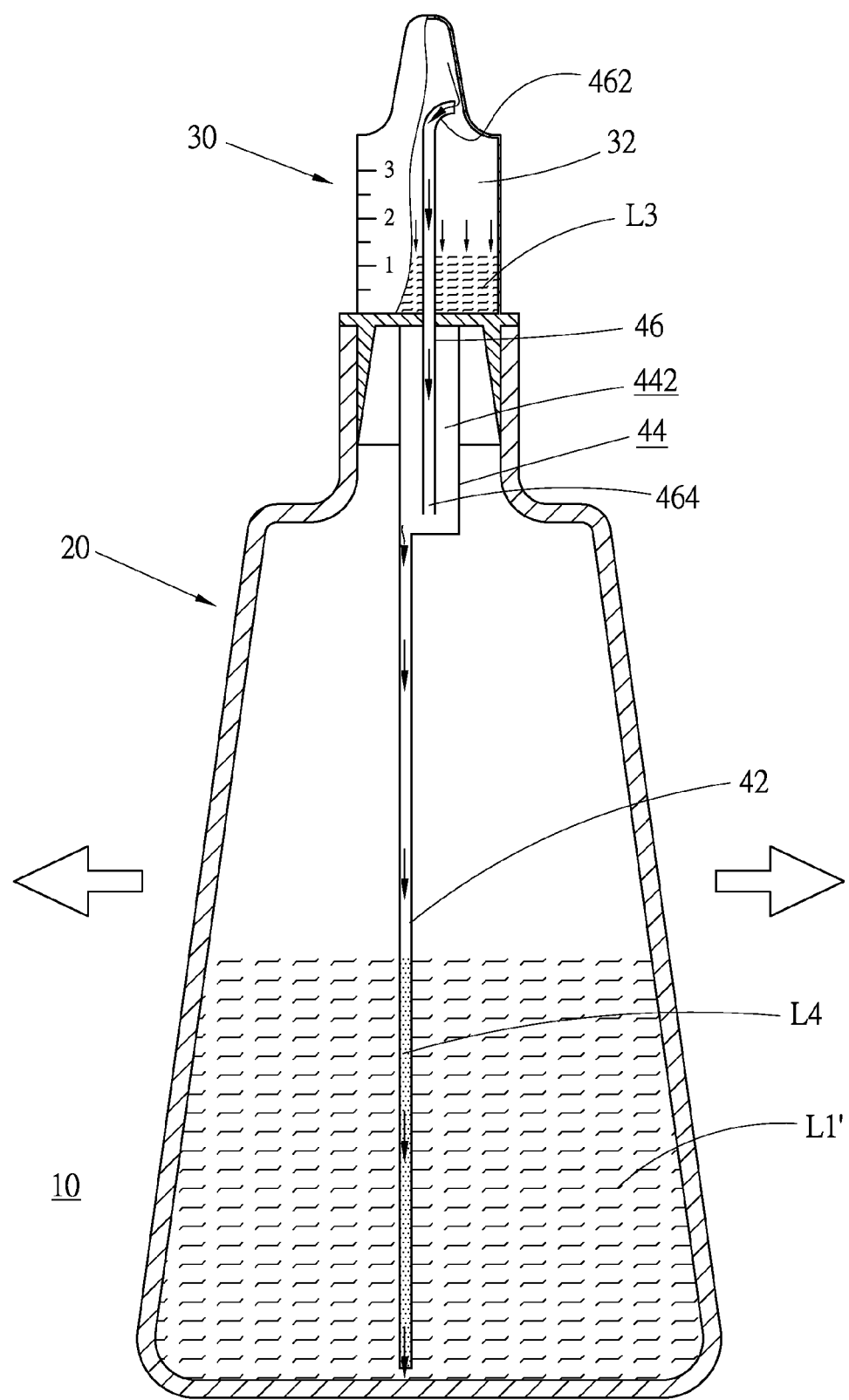

Referring to FIG. 3B, after the amount of the liquid L3 contained in the liquid reservoir 32 of the nozzle 30 reaches a desired dose, the resilient bottle body 20 is released from the compression force. At this time, the internal air pressure is lower than the external air pressure, whereby the external air backward flows in the flow path P from the exterior to refill into the resilient bottle body 20. Accordingly, the amount of the liquid L3 contained in the nozzle 30 to be dispensed can keep constant. Also, the liquid temporarily reserved in the flow path P as shown in FIG. 3A is backward driven by the air to flow back into the bottle body 20 without residue in the flow path P. The flowing back liquid refills into the bottle body 20 to together form a certain amount of liquid L1'. Based on the U-tube principle, a certain amount of liquid L4 still remains in a lower section of the first transfer pipe 42 and levels at the liquid L1'.

Figure 3C:
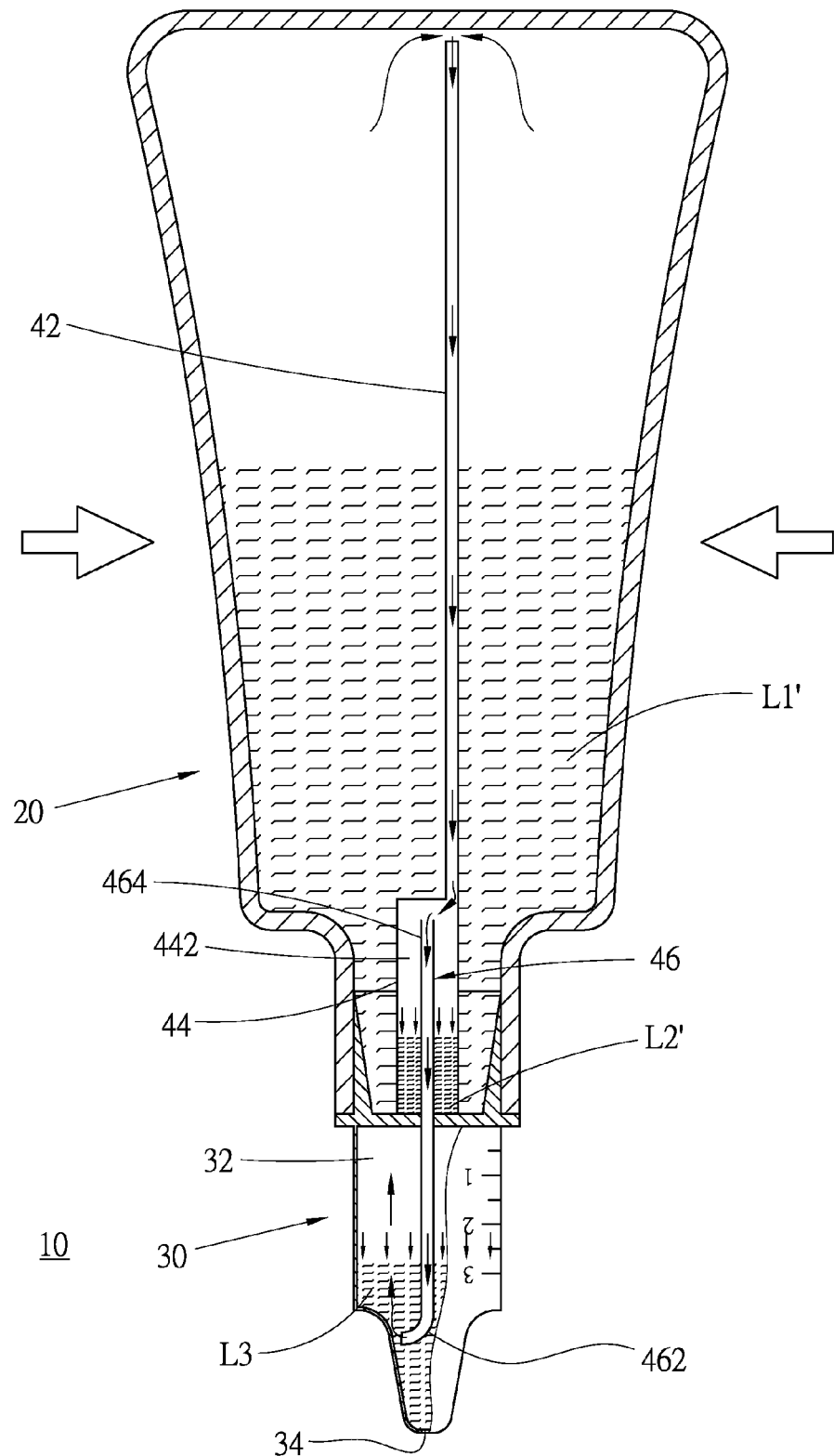

Referring to FIG. 3C, when the dropper structure 10 is reserved, the constant amount of liquid L3 contained in the nozzle 30 flows to a position of low potential energy. The liquid L4 flows along the first transfer pipe 42 into the remaining liquid reservoir 44 to form a certain amount of remaining liquid L2'. The remaining liquid L2' will not mix with the constant amount of liquid L3, which has been contained in the nozzle 30. Then the bottle body 20 is compressed to drive the air in the bottle body to forward flow along the flow path P to the nozzle 30. The air then drives the constant amount of liquid L3 to be dispensed from the dispensing orifice 34.

Figure 3D:
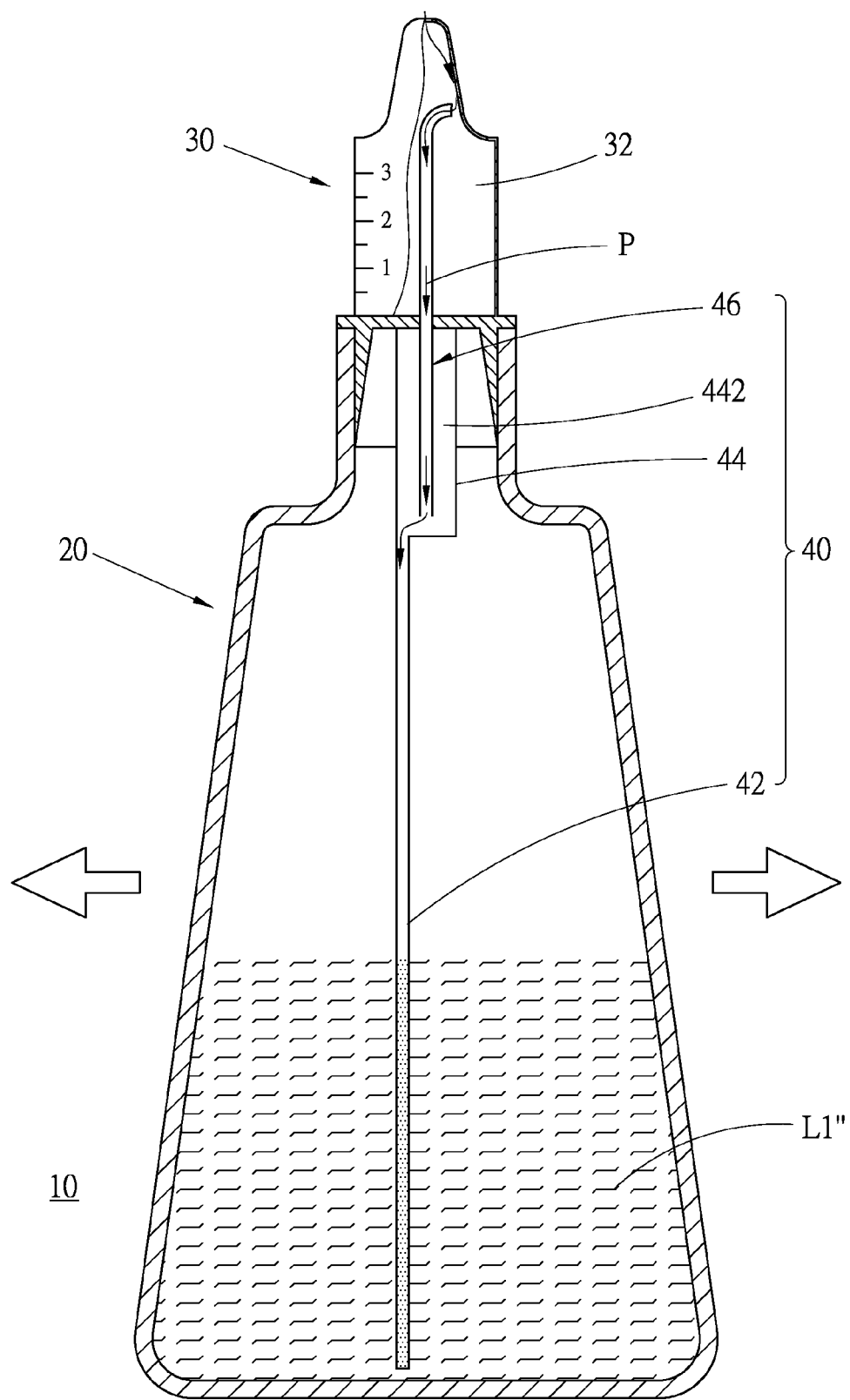

Referring to FIG. 3D, when the dropper structure 10 is restored to an upright position, the remaining liquid L2' contained in the remaining liquid reservoir 44 flows along the first transfer pipe 42 back into the bottle body 20 as the liquid L1". Then, the resilient bottle body 20 is released from the compression force. At this time, the external air again backward flows from the exterior to refill into the resilient bottle body 20 without liquid residue in the transfer mechanism 40.

In the dropper structure 10 according to the present invention, the remaining liquid L2' is temporarily reserved in the remaining liquid chamber 442 without hazards of mixing with the constant amount of liquid L3 contained in the nozzle 30. Therefore, the dose of the liquid L3 will not be affected so that the droplets can be quantitatively dispensed at constant amount under precise control.

With a conventional dropper, a user needs to troublesomely repeatedly compress the bottle body of the dropper and count the number of times of compression with attention for dispensing a larger dose. In contrast, in the dropper structure 10 according to the present invention, a user can first accumulate the liquid in the nozzle 30 to a desired dose and then dispense the liquid at one time. Accordingly, it is unnecessary for the user to troublesomely count the number of times of compression. Also, it is unnecessary for the user to pay too much attention to the magnitude of the compression force. Therefore, the possibility of improper dosage can be minimized. Moreover, a larger amount of liquid can be constantly dispensed at one time to greatly reduce the use of the burette and graduated cup. According to the above, the dropper structure 10 of the preferred embodiment of the present invention can dispense a precise dose of liquid and can be conveniently used.

The remaining liquid reservoir 44 serves to contain the remaining liquid therein. Preferably, the remaining liquid reservoir 44 is arranged in a position near the nozzle 30. Also, the second transfer pipe 46 of the transfer mechanism 40 is preferably disposed in a position distal from the liquid level in the bottle body 20. In the first embodiment, the remaining liquid reservoir 44 is connected under the bottom wall of the nozzle 30. Preferably, the remaining liquid reservoir 44 has a diameter slightly smaller than that of the bottle opening 24 and is spaced from the fitting section 38 of the nozzle 30. Optionally, the remaining liquid reservoir 44 can be integrally connected with the nozzle 30 to ensure that the nozzle 30 is seamlessly connected with the transfer mechanism 40. In this case, the air is prevented from escaping so that the use of the dropper structure will not be affected.

Figure 4:
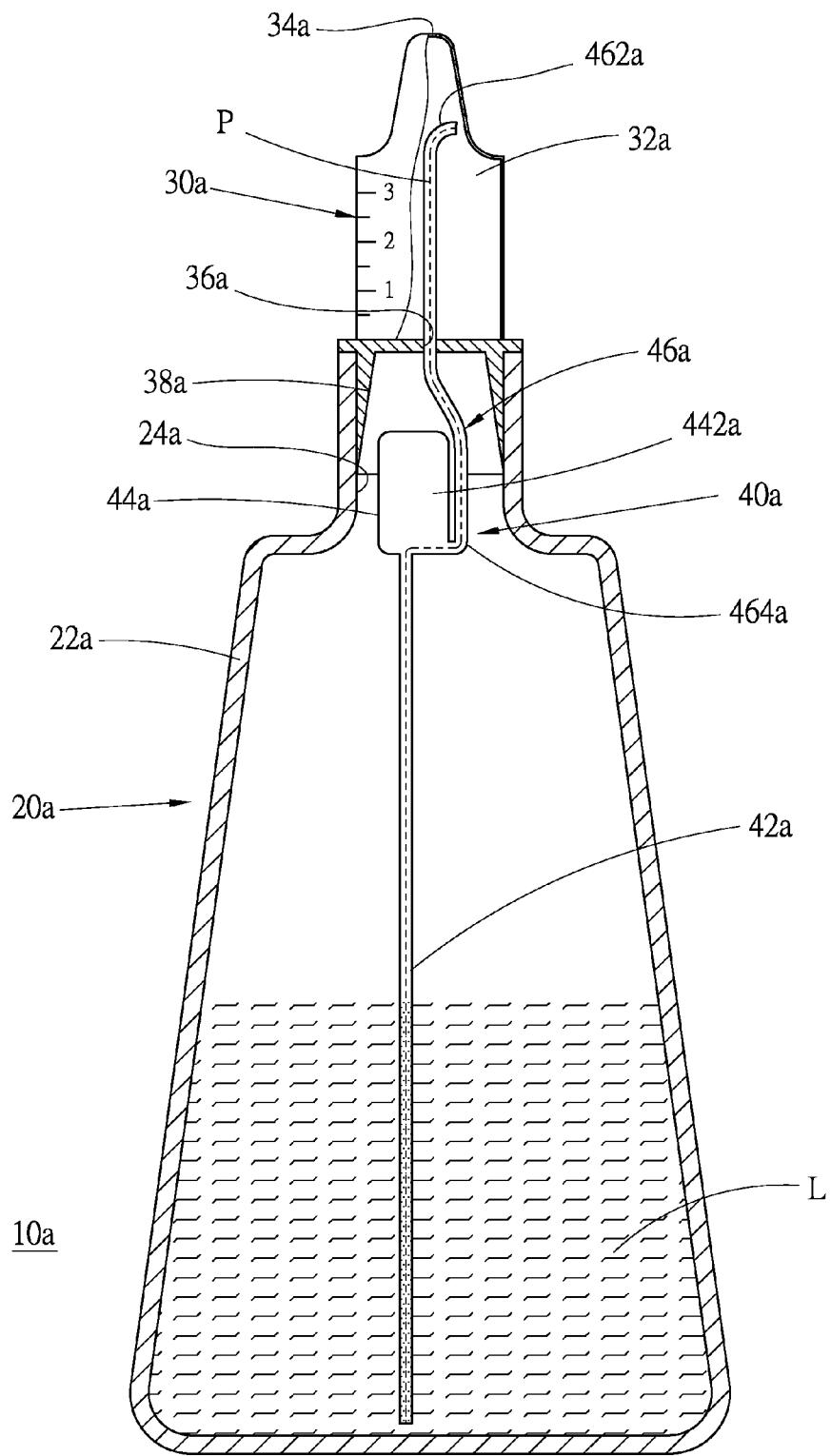
FIG. 4 is a sectional view of a second embodiment of the quantitative dropper structure according to the present invention.

FIG. 4 shows a second embodiment of the present invention, in which the remaining liquid reservoir 44a is suspended in the bottle body, not connected to the nozzle 30a, while still is arranged in a position near the nozzle 30a. In addition, in order to have better space utilization efficiency, the remaining liquid reservoir can be partially disposed in the nozzle (not shown) in a form different from that of FIGS. 1 and 4.

Further referring to FIG. 4, in the second embodiment, the second transfer pipe 46a has a configuration different from the first embodiment. The second transfer pipe 46a at least has a front end 462a and a rear end 464a. The front end 462a passes through the perforation 36a of the bottom wall of the nozzle 30a and extends into the liquid reservoir 32a of the nozzle 30a. The second transfer pipe 46a is disposed outside and alongside the remaining liquid reservoir 44a with the rear end 464a positioned outside the remaining liquid reservoir 44a. The rear end 464a is connected to a circumference of a bottom end of the remaining liquid reservoir 44a in communication with the remaining liquid chamber 442a. According to the second embodiment as shown in FIG. 4, the specifically configured second transfer pipe and remaining liquid reservoir can be applied to the dropper structure at the same time.

Figure 5:
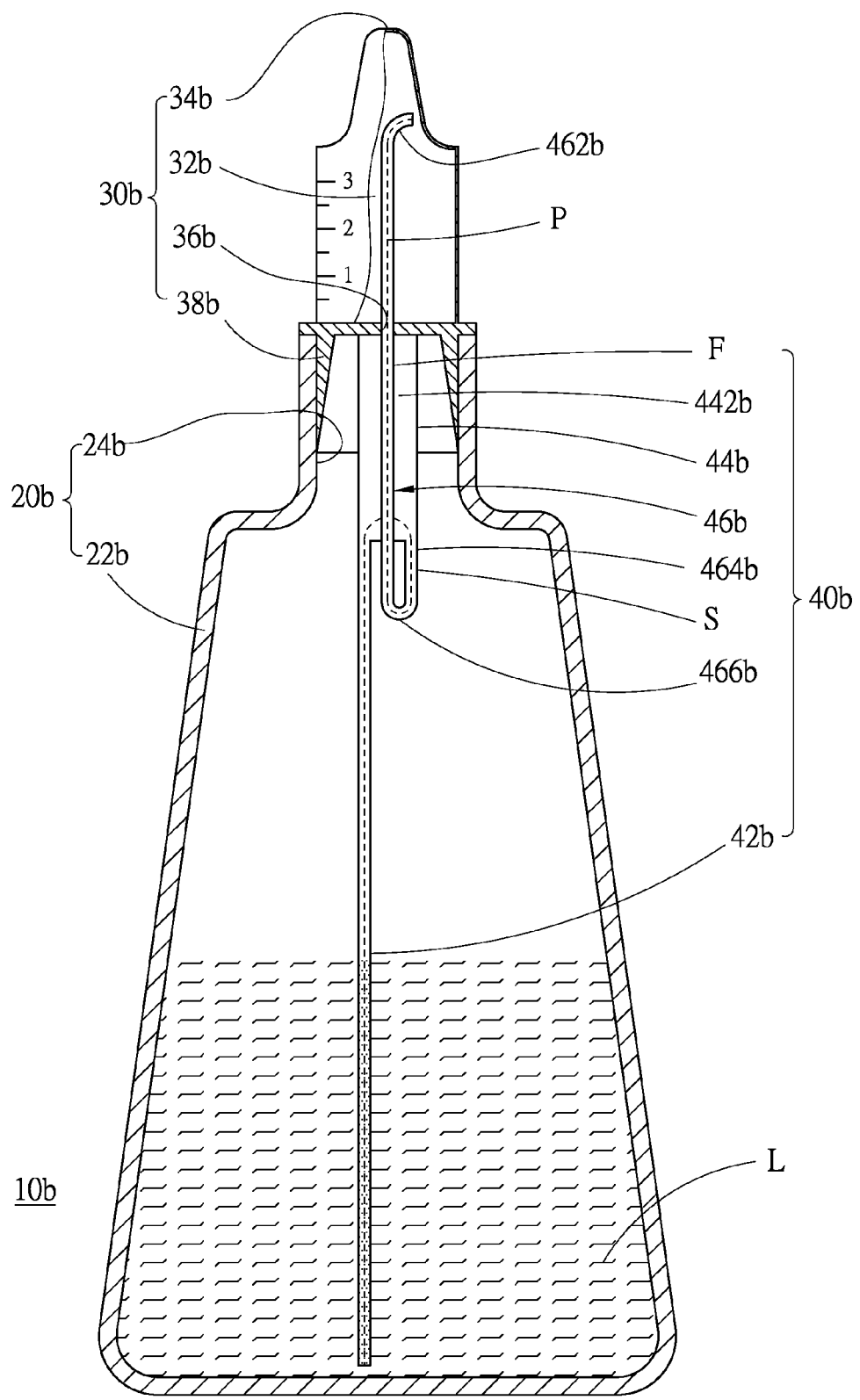
FIG. 5 is a sectional view of a third embodiment of the quantitative dropper structure according to the present invention.
Figure 6:
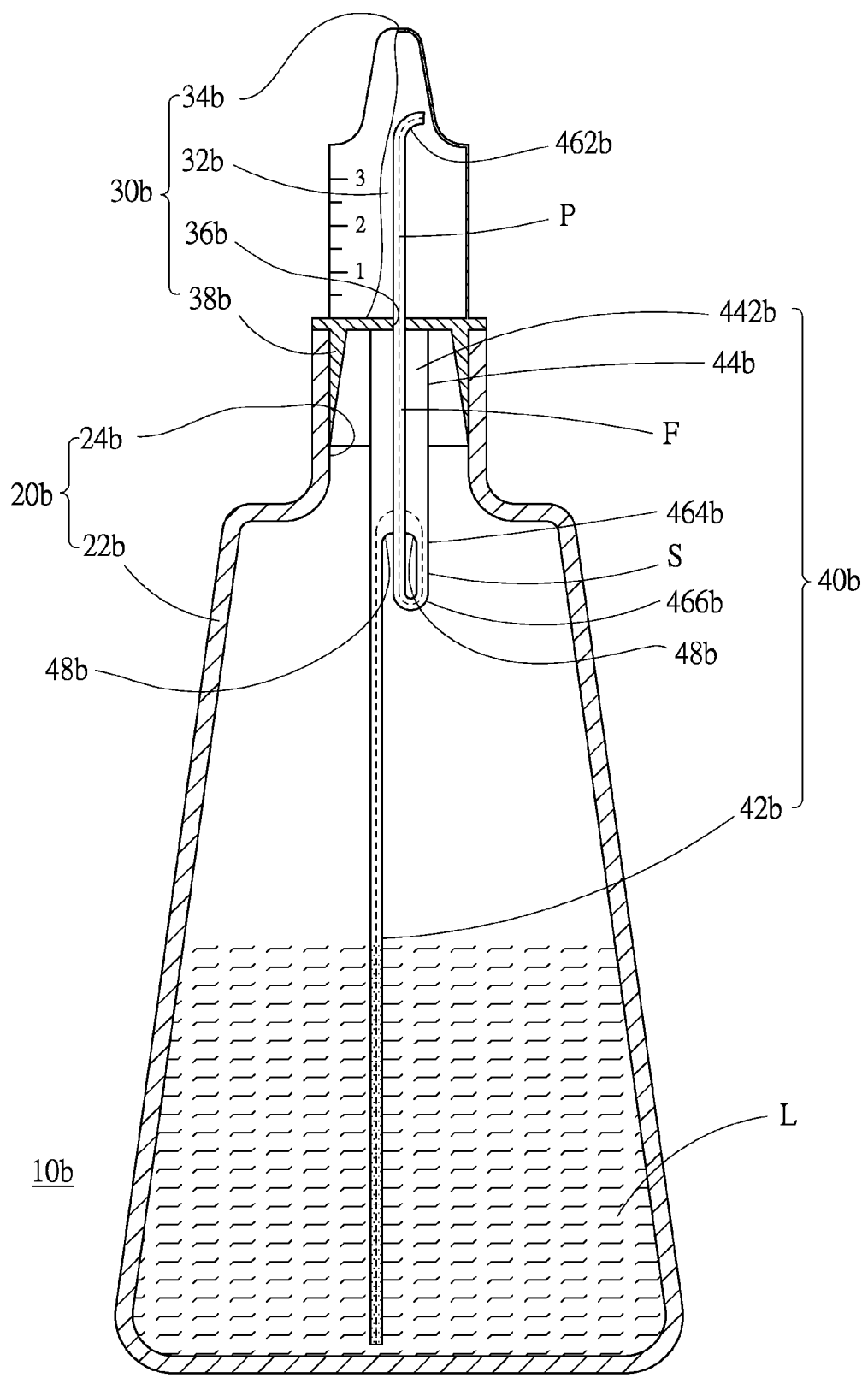
FIG. 6 is a sectional view according to FIG. 5, in which the transfer mechanism has a different configuration.

FIG. 5 shows a third embodiment of the present invention, in which the components are substantially structurally identical to those of the first embodiment. The third embodiment is different from the first embodiment in that the second transfer pipe 46b is substantially U-shaped, including a first section F, a second section S and a bight section 466b connected between the first and second sections. The first section F has a free end as the front end 462b of the second transfer pipe. The second section S has a rear end as the rear end 464b of the second transfer pipe. The first section F passes through the remaining liquid reservoir 44b and the perforation 36b of the bottom wall of the nozzle 30b with the front end 462b extending into the liquid reservoir 32b of the nozzle 30b. The rear end 464b is positioned outside the remaining liquid reservoir 44b and connected to a bottom face of the remaining liquid reservoir 44b in communication with the remaining liquid chamber 442b. Referring to FIG. 6, the bottom wall of the remaining liquid reservoir 44b of the transfer mechanism 40b is formed with at least one guide face 48b. The guide face 48b is positioned between a communication point between the first transfer pipe 42b and the bottom wall of the remaining liquid reservoir 44b and/or a communication point between the second transfer pipe 46b and the bottom wall of the remaining liquid reservoir 44b. The configuration of the guide face 48b is not specifically limited. The guide face 48b mainly serves to make the liquid more easily flow through the remaining liquid reservoir 44b to minimize the possibility of liquid residue (in the bight section 466b).

Please refer to FIGS. 7A to 7E, which show the use of the third embodiment of the quantitative dropper structure (with the bight section 466b) of the present invention.

Figure 7A:
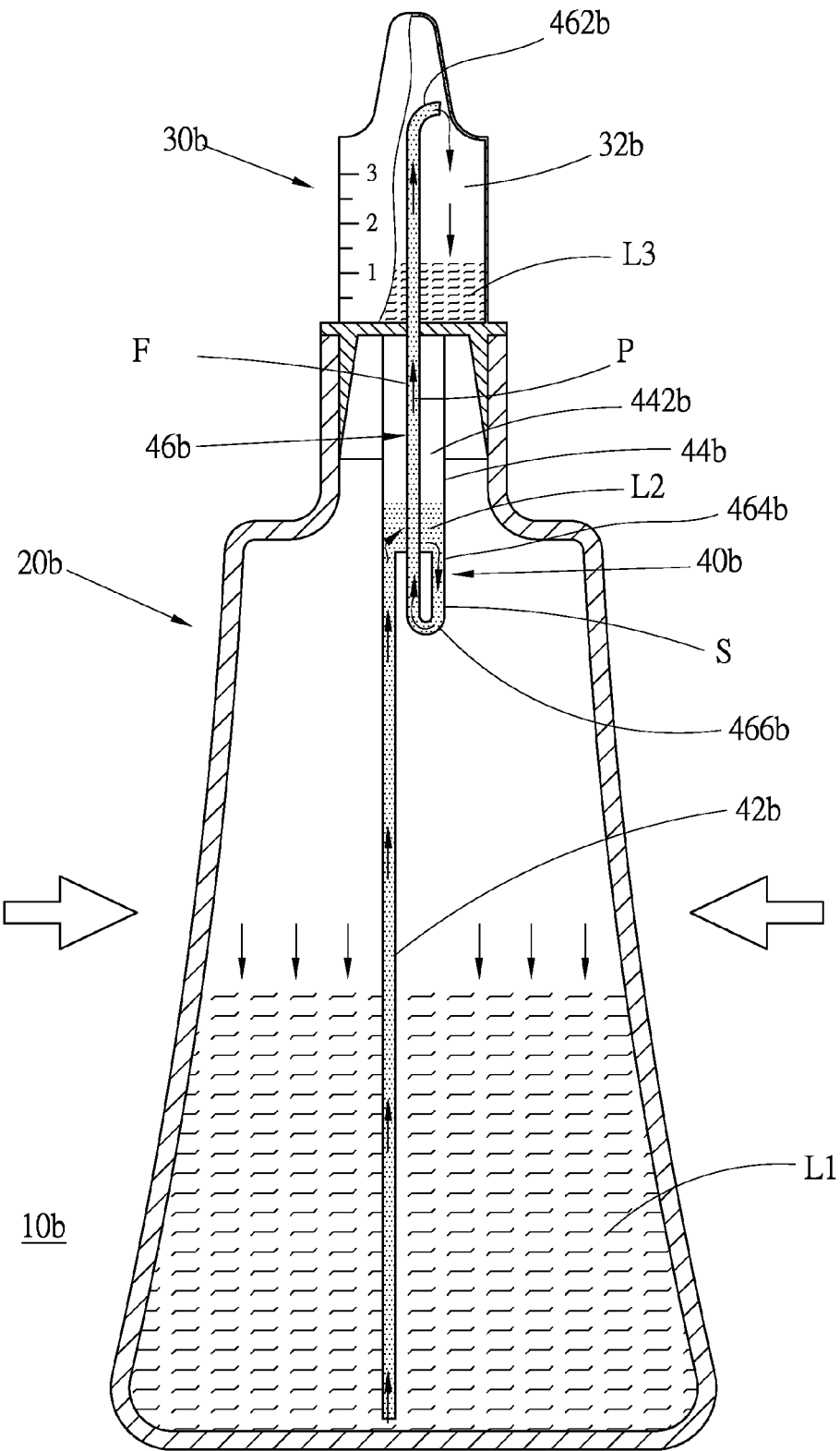
FIGS. 7A to 7E show the use of the third embodiment of the quantitative dropper structure according to the present invention.

As shown in FIG. 7A, when compressing the resilient bottle body 20b, the air inside the bottle body 20b is pressurized to drive the liquid L1 and make the liquid L1 forward flow in the flow path P into the liquid reservoir 32b of the nozzle 30b. During the flowing of the liquid, a certain amount of flowing liquid L2 is reserved in the remaining liquid chamber 442b of the remaining liquid reservoir 44b. A user can observe the scales of the nozzle 30b to truly know the volume of the liquid L3 to be dispensed.

Figure 7B:
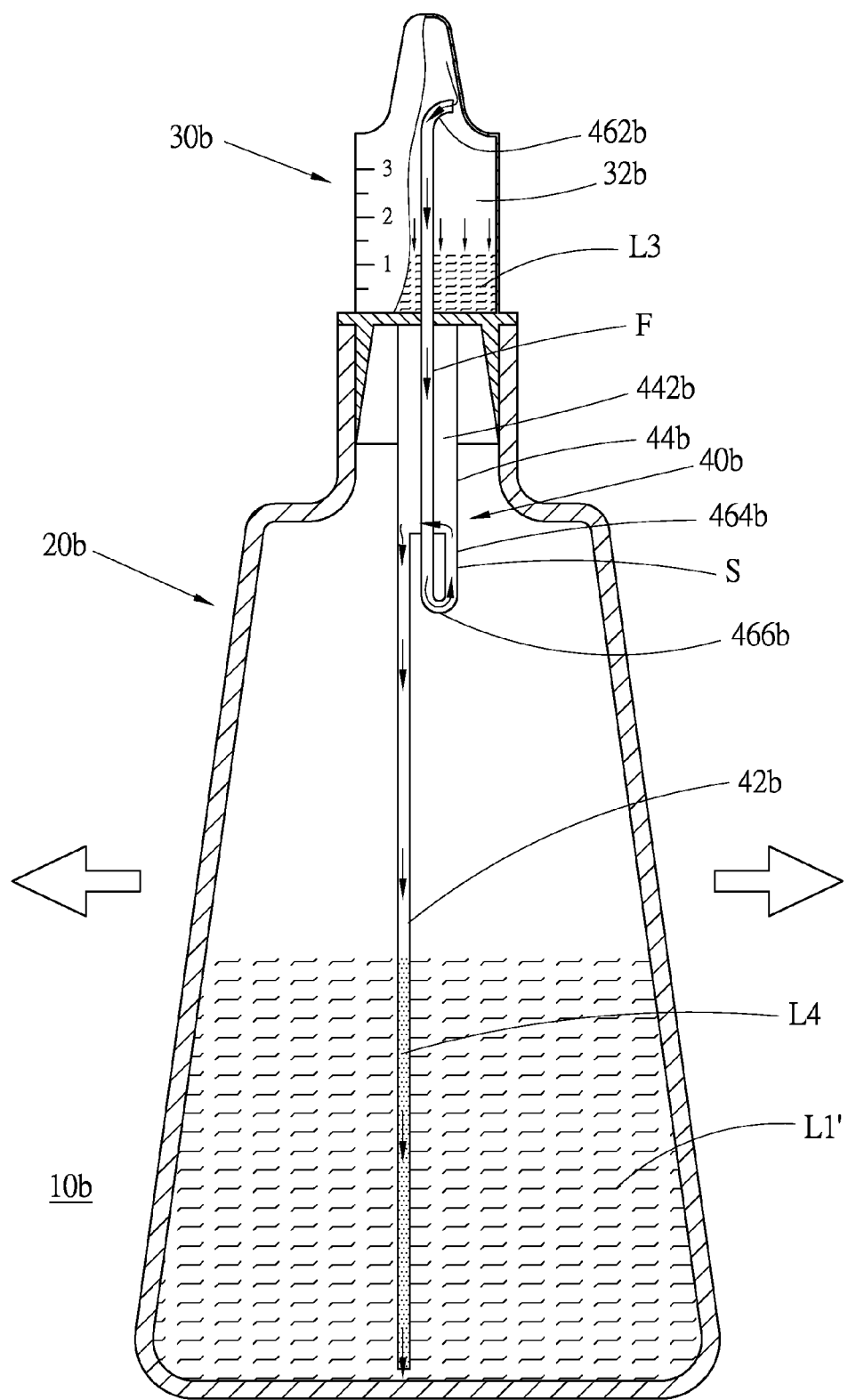

Referring to FIG. 7B, after the amount of the liquid L3 reaches a desired dose, the resilient bottle body 20b is released from the pressure. At this time, the external air backward flows in the flow path P from the exterior to refill into the resilient bottle body 20b. Accordingly, the amount of the liquid L3 contained in the nozzle 30b to be dispensed can keep constant. Also, the liquid temporarily reserved in the flow path P as shown in FIG. 7A is backward driven by the air to flow back into the bottle body 20b without residue in the flow path P. The flowing back liquid refills into the bottle body 20b to together form a certain amount of liquid L1'. Based on the U-tube principle, a certain amount of liquid L4 still remains in a lower section of the first transfer pipe 42b and levels at the liquid L1'.

Figure 7C:
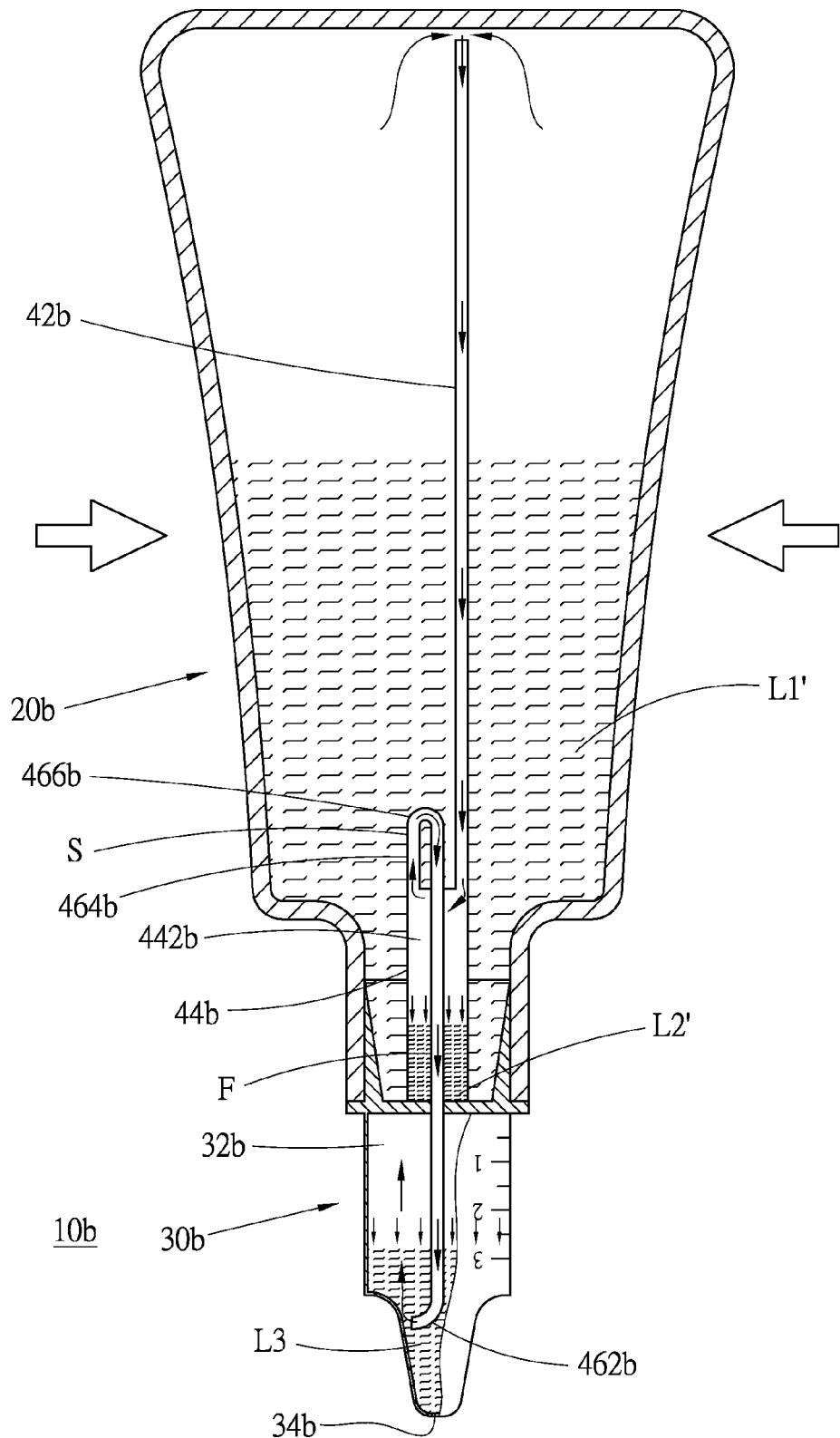

Referring to FIG. 7C, when the dropper structure 10b is reserved, the liquid L4 flows into the remaining liquid reservoir 44b to form a certain amount of remaining liquid L2'. The remaining liquid L2' will not mix with the constant amount of liquid L3 contained in the nozzle 30b. Then the bottle body 20b is compressed to drive the air in the bottle body to forward flow in the flow path P to the nozzle 30b. The air then drives the constant amount of liquid L3 to be dispensed from the dispensing orifice 34b.

Figure 7D:
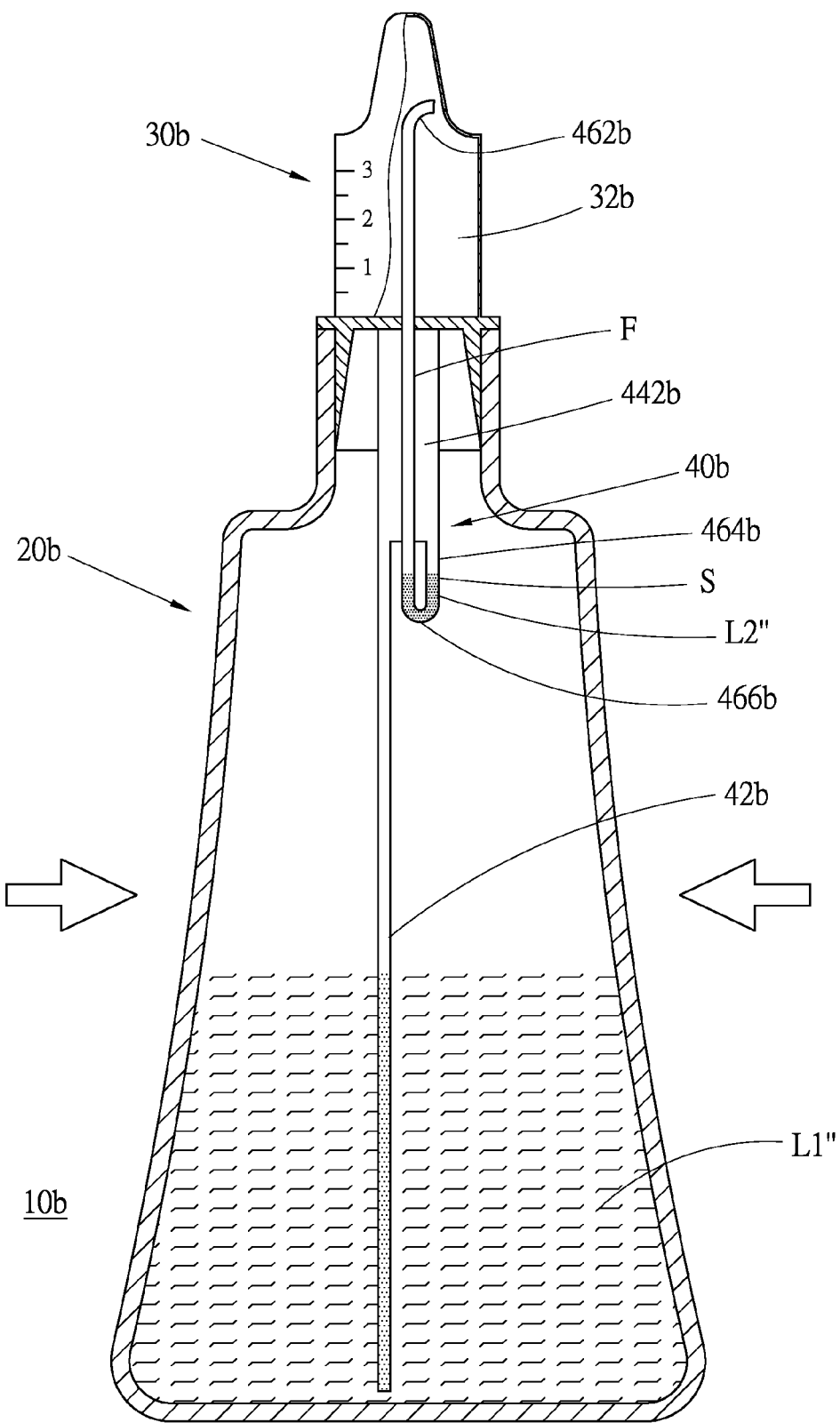

Referring to FIG. 7D, when the dropper structure 10b is restored to an upright position, the remaining liquid L2' contained in the remaining liquid reservoir 44b partially flows back to the bight section 466b of the second transfer pipe 46b as remaining liquid L2" and partially flows along the first transfer pipe 42b back into the bottle body 20b as the liquid L1".

Figure 7E:
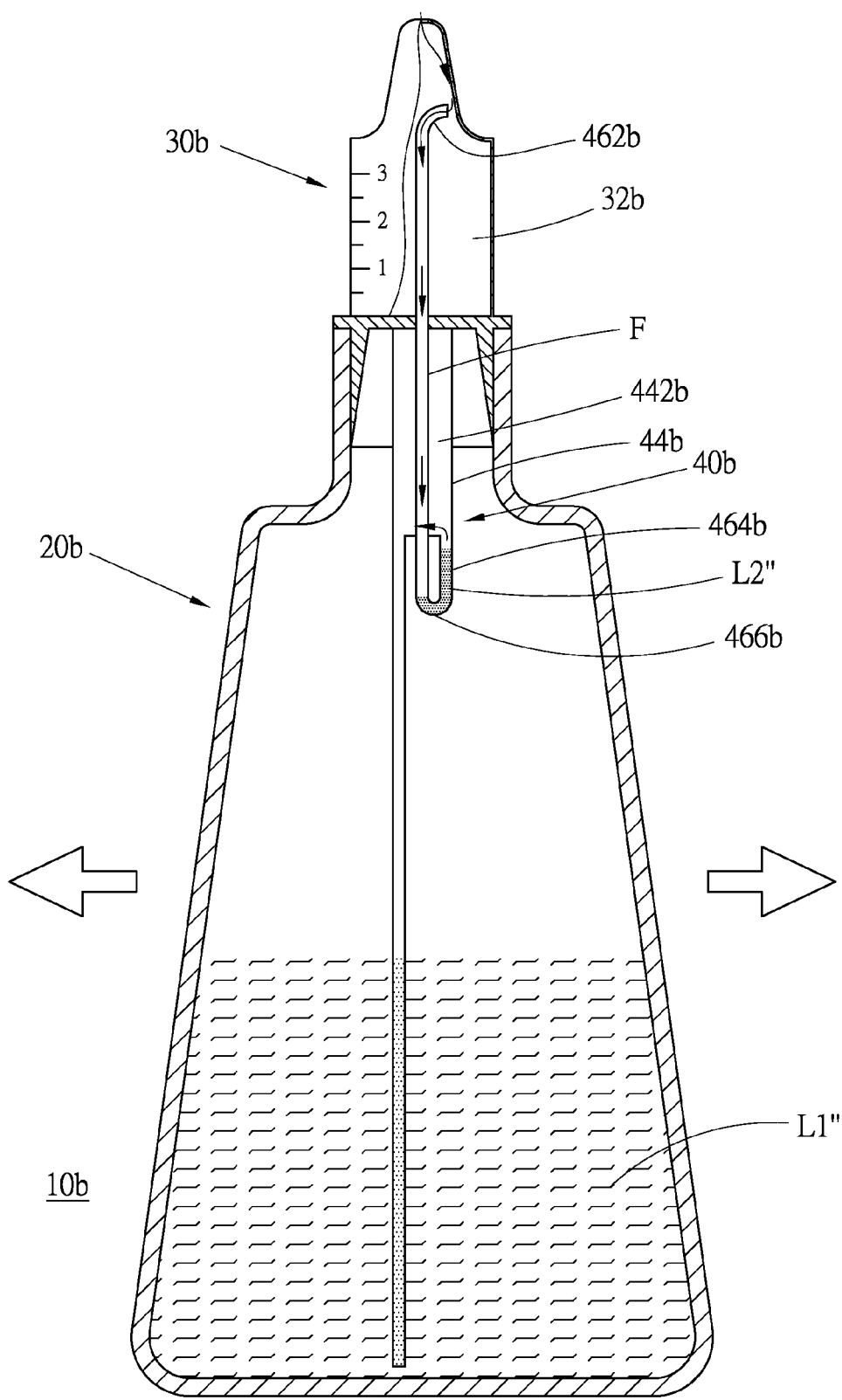

Then, the resilient bottle body 20b is released from the compression force. At this time, the internal air pressure is lower than the external air pressure, whereby the external air backward flows in the flow path P from the exterior into the resilient bottle body 20b as shown in FIG. 7E. In this case, the liquid L2" remaining in the bight section 466b will be driven back into the bottle body 20b.

Figure 8:
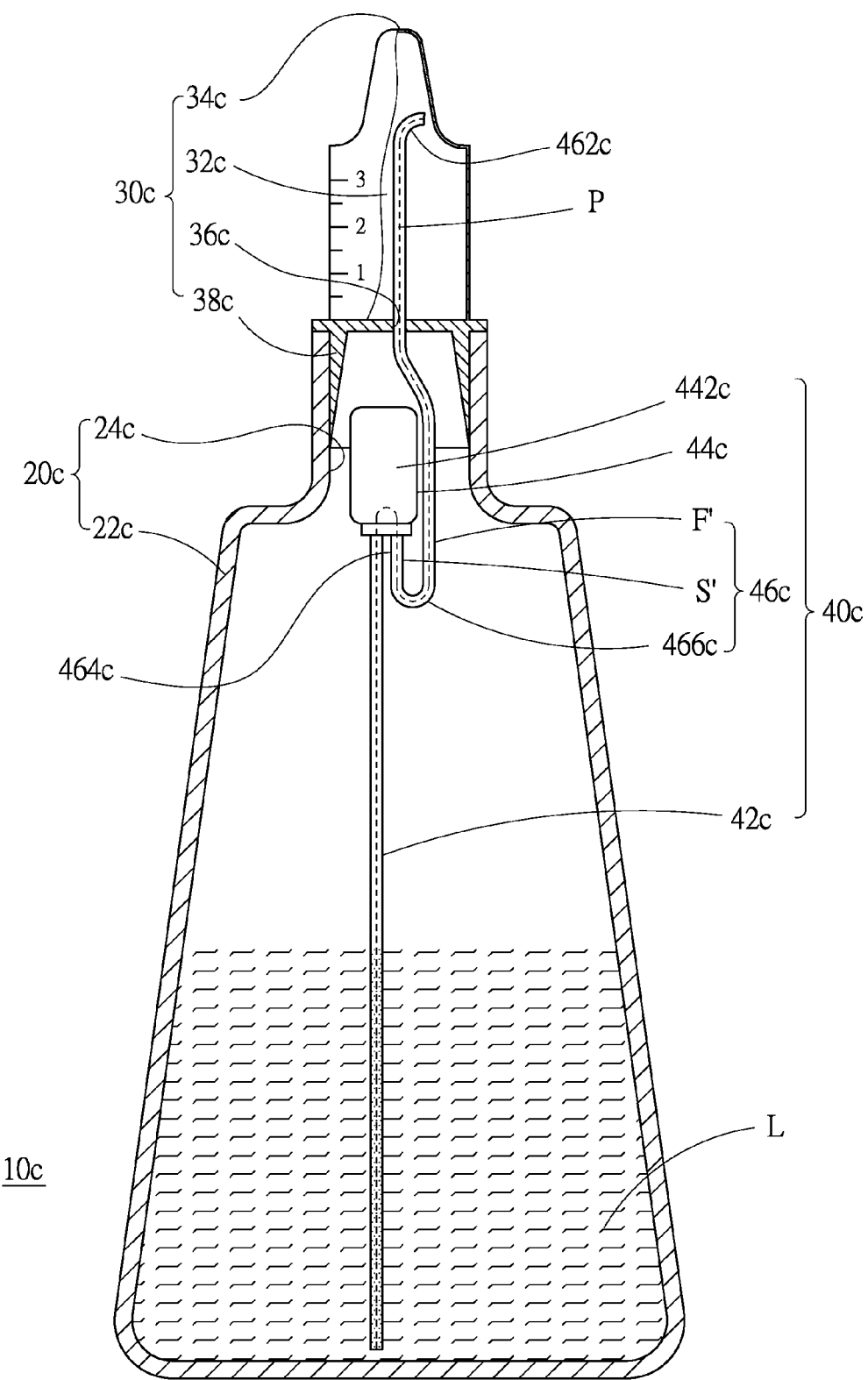
FIG. 8 is a sectional view of a fourth embodiment of the quantitative dropper structure according to the present invention.

FIG. 8 shows a fourth embodiment of the present invention, in which the components are substantially structurally identical to those of the third embodiment. The second transfer pipe 46c of the fourth embodiment has a configuration different from that of the third embodiment. The second transfer pipe 46c has a first section F' disposed outside and alongside the remaining liquid reservoir 44c without passing therethrough. The front end 462c of the second transfer pipe 46c also passes through the perforation 36c of the bottom wall of the nozzle 30c and extends into the liquid reservoir 32c. The first section F' can be suspended in the bottle body 20c or connected to an outer face of the remaining liquid reservoir 44c to enhance stability.

The dropper structure is a squeeze dropping bottle made of resilient material such as PVC. The nozzle is transparent or at least translucent for a user to observe and check the dose of the liquid contained in the nozzle.

The above embodiments are only used to illustrate the present invention, not intended to limit the scope thereof Many modifications of the above embodiments can be made without departing from the spirit of the present invention.

What is claimed is:

1. A quantitative dropper structure comprising:
    a resilient bottle body being compressible and having a bottle opening at a top end thereof;
    a nozzle detachably and sealingly connected to the bottle opening, the nozzle being formed with a liquid reservoir for containing a liquid therein, the nozzle being transparent or translucent for a user to observe and check the volume of the liquid contained in the nozzle, the nozzle having a tip formed with a dispensing orifice, the nozzle further having a bottom wall formed with a perforation; and
    a transfer mechanism received in the bottle body and connected to the nozzle, the transfer mechanism having a flow path formed of a first transfer pipe, a remaining liquid reservoir and a second transfer pipe, wherein:
    the remaining liquid reservoir is formed with an internal remaining liquid chamber for containing remaining liquid therein;
    the first transfer pipe is positioned outside the remaining liquid reservoir, a top end of the first transfer pipe being connected to the remaining liquid reservoir in communication with the remaining liquid chamber, a bottom end of the first transfer pipe downward extending to a position near a bottom section of the bottle body; and
    the second transfer pipe at least has a front end and a rear end, the front end passing through the perforation of the bottom wall of the nozzle and extending into the liquid reservoir thereof, the rear end extending into the remaining liquid reservoir to a position near the bottom wall thereof in communication with the remaining liquid chamber, whereby when compressing the bottle body, the liquid is driven to forward flow in the flow path into the liquid reservoir of the nozzle, after a necessary dose of liquid is contained in the liquid reservoir of the nozzle, the liquid is quantitatively dispensed from the dispensing orifice at constant amount.

2. The quantitative dropper structure as claimed in claim 1, wherein the front end of the second transfer pipe extends from the remaining liquid chamber through the perforation of the bottom wall of the nozzle to communicate with the liquid reservoir thereof.

3. The quantitative dropper structure as claimed in claim 1, wherein the front end of the second transfer pipe is curved toward an inner face of the nozzle.

4. The quantitative dropper structure as claimed in claim 1, wherein an exit of the front end of the second transfer pipe is not positioned right below the dispensing orifice of the nozzle.

5. The quantitative dropper structure as claimed in claim 1, wherein a circumference of the nozzle is marked with scales.

6. The quantitative dropper structure as claimed in claim 1, wherein a fitting section is formed under the bottom wall of the nozzle for fitting into the bottle opening of the bottle body.

7. A quantitative dropper structure comprising:
    a resilient bottle body being compressible and having a bottle opening at a top end of the resilient bottle body;
    a nozzle detachably and sealingly connected to the bottle opening, the nozzle being formed with a liquid reservoir for containing a liquid therein, the nozzle being transparent or translucent for a user to observe and check the volume of the liquid contained in the nozzle, the nozzle having a tip formed with a dispensing orifice, the nozzle further having a bottom wall formed with a perforation; and
    a transfer mechanism received in the bottle body and connected to the nozzle, the transfer mechanism having a flow path formed of a first transfer pipe, a remaining liquid reservoir and a second transfer pipe, wherein:
    the remaining liquid reservoir is formed with an internal remaining liquid chamber for containing remaining liquid therein;
    the first transfer pipe is positioned outside the remaining liquid reservoir, a top end of the first transfer pipe being connected to the remaining liquid reservoir in communication with the remaining liquid chamber, a bottom end of the first transfer pipe downward extending to a position near a bottom section of the bottle body; and
    the second transfer pipe at least has a front end and a rear end, the front end passing through the perforation of the bottom wall of the nozzle and extending into the liquid reservoir thereof, the rear end being positioned outside the remaining liquid reservoir and connected to a bottom end thereof in communication with the remaining liquid chamber, whereby when compressing the bottle body, the liquid is driven to forward flow in the flow path into the liquid reservoir of the nozzle, after a necessary dose of liquid is contained in the liquid reservoir of the nozzle, the liquid is quantitatively dispensed from the dispensing orifice at constant amount.

8. The quantitative dropper structure as claimed in claim 7, wherein the second transfer pipe is disposed outside and alongside the remaining liquid reservoir.

9. The quantitative dropper structure as claimed in claim 7, wherein the front end of the second transfer pipe is curved toward an inner face of the nozzle.

10. The quantitative dropper structure as claimed in claim 7, wherein an exit of the front end of the second transfer pipe is not positioned right below the dispensing orifice of the nozzle.

11. The quantitative dropper structure as claimed in claim 7, wherein a circumference of the nozzle is marked with scales.

12. The quantitative dropper structure as claimed in claim 7, wherein a fitting section is formed under the bottom wall of the nozzle for fitting into the bottle opening of the bottle body.

13. A quantitative dropper structure comprising:
    a resilient bottle body being compressible and having a bottle opening at a top end of the resilient bottle body;
    a nozzle detachably and sealingly connected to the bottle opening, the nozzle being formed with a liquid reservoir for containing a liquid therein, the nozzle being transparent or translucent for a user to observe and check the volume of the liquid contained in the nozzle, the nozzle having a tip formed with a dispensing orifice, the nozzle further having a bottom wall formed with a perforation; and a transfer mechanism received in the bottle body and connected to the nozzle, the transfer mechanism having a flow path formed of a first transfer pipe, a remaining liquid reservoir and a second transfer pipe, wherein:

the remaining liquid reservoir is formed with an internal remaining liquid chamber for containing remaining liquid therein;

the first transfer pipe is positioned outside the remaining liquid reservoir, a top end of the first transfer pipe being connected to the remaining liquid reservoir in communication with the remaining liquid chamber, a bottom end of the first transfer pipe downward extending to a position near a bottom section of the bottle body; and the second transfer pipe has a first section, a second section and a bight section connected between the first and second sections, the first section having a free end as a front end of the second transfer pipe, the second section having a rear end as a rear end of the second transfer pipe, the front end of the second transfer pipe passing through the perforation of the bottom wall of the nozzle and extending into the liquid reservoir of the nozzle, the rear end of the second transfer pipe being positioned outside the remaining liquid reservoir and connected to a bottom face of the remaining liquid reservoir in communication with the remaining liquid chamber, whereby when compressing the bottle body, the liquid is driven to forward flow in the flow path into the liquid reservoir of the nozzle, after a necessary dose of liquid is contained in the liquid reservoir of the nozzle, the liquid is quantitatively dispensed from the dispensing orifice at constant amount.

14. The quantitative dropper structure as claimed in claim 13, wherein the first section of the second transfer pipe passes through the remaining liquid reservoir and extends through the perforation of the bottom wall of the nozzle into the liquid reservoir thereof.

15. The quantitative dropper structure as claimed in claim 13, wherein the first section of the second transfer pipe is disposed outside and alongside the remaining liquid reservoir.

16. The quantitative dropper structure as claimed in claim 13, wherein the front end of the second transfer pipe is curved toward an inner face of the nozzle.

17. The quantitative dropper structure as claimed in claim 13, wherein an exit of the front end of the second transfer pipe is not positioned right below the dispensing orifice of the nozzle.

18. The quantitative dropper structure as claimed in claim 13, wherein a circumference of the nozzle is marked with scales.

19. The quantitative dropper structure as claimed in claim 13, wherein a fitting section is formed under the bottom wall of the nozzle for fitting into the bottle opening of the bottle body.

20. The quantitative dropper structure as claimed in claim 13, wherein the bottom wall of the remaining liquid reservoir is formed with at least one guide face, which is positioned at a communication point between the first transfer pipe and the second transfer pipe.

* * * * *